United States Patent [19]

Maekawa et al.

[11] 4,451,662
[45] May 29, 1984

[54] PROCESS FOR PREPARING 2,3-DIHYDRO-2,2-DIMETHYL-7-HYDROXYBENZOFURAN

[75] Inventors: Tsukasa Maekawa; Takeshi Gondo, both of Tokushima, Japan

[73] Assignee: Otsuka Kagaku Yakuhin Kabushiki Kaisha, Japan

[21] Appl. No.: 387,604

[22] Filed: Jun. 11, 1982

[30] Foreign Application Priority Data

Sep. 1, 1981 [JP] Japan .................................. 56-138240
Apr. 7, 1982 [JP] Japan .................................. 57-58745

[51] Int. Cl.³ .......................................... C07D 307/86
[52] U.S. Cl. .................................................. 549/462
[58] Field of Search .......................................... 549/462

[56] References Cited

U.S. PATENT DOCUMENTS

| | | | |
|---|---|---|---|
| 3,474,170 | 10/1969 | Scharpf | 424/285 |
| 3,474,171 | 10/1969 | Scharpf | 424/285 |
| 3,876,667 | 4/1975 | Serban et al. | 549/462 |
| 4,256,647 | 3/1981 | Michelet et al. | 549/462 |
| 4,297,284 | 10/1981 | Michelet | 549/462 |
| 4,380,654 | 4/1983 | Franko-Filipasic et al. | 549/462 |

FOREIGN PATENT DOCUMENTS 2932458 2/1981 Fed. Rep. of Germany .

Primary Examiner—Henry R. Jilen
Assistant Examiner—Bernard Dentz
Attorney, Agent, or Firm—Larson and Taylor

[57] ABSTRACT

A process for preparing 2,3-dihydro-2,2-dimethyl-7-hydroxybenzofuran which comprises subjecting o-methallyloxyphenol to a rearrangement and cyclization reactions in the presence of, as a catalyst, aluminum halide and N-substituted aniline derivative, or a complex of both these compounds.

10 Claims, No Drawings

PROCESS FOR PREPARING 2,3-DIHYDRO-2,2-DIMETHYL-7-HYDROXYBENZOFURAN

This invention relates to a process for preparing 2,3-dihydro-2,2-dimethyl-7-hydroxybenzofuran using, as a starting material, o-methallyloxyphenol.

2,3-Dihydro-2,2-dimethyl-7-hydroxybenzofuran is a known compound as a starting material of carbofuran insecticide. It is known that carbofuran is prepared by methyl carbamation of this compound.

Many processes have been conventionally developed to prepare 2,3-dihydro-2,2-dimethyl-7-hydroxybenzofuran (hereinafter referred to as "benzofuranol") by use of, as a starting material, o-methallyloxyphenol (hereinafter referred to as "monoether").

Generally, benzofuranol was prepared by heating the monoether at about 200° C. as disclosed in Japanese Examined Patent (hereinafter referred to as "Kokoku") No. 7,223/1966 and Kokoku No. 12,263/1967 (U.S. Pat. No. 3,474,171) but yields were below 50%. Thereafter, many improved methods were investigated. Japanese Unexamined Patent (hereinafter referred to as "Kokai") No. 76,870/1980 (U.S. Pat. No. 4,256,647) discloses a process of heating the monoether at 170° to 230° C. in the presence of water and optionally in the presence of an inert organic solvent, Kokai No. 16,484/1981 (U.S. Pat. No. 4,297,284) a process of heating isobutenyl-pyrocatechol or isobutenylpyrocatechol/methallyl-pyrocatechol admixture at 60° to 200° C. in the presence of an organic sulfonic acid and Kokai No. 29,584/1981 (DT-OS 2,932,458) a process of etherification of pyrocatechol, rearrangement and cyclization in the presence of a specific polyhydroxyalkyl ether. However, these conventional processes involve disadvantages that the yields of benzofuranol are low, a specific solvent must be used, reactions have to be conducted at high pressures, etc.

An object of the invention is to provide a process for preparing benzofuranol from the monoether economically with an increased total yield of benzofuranol.

Another object of the invention is to provide a process for preparing benzofuranol from the monoether economically with use of a usual and inexpensive solvent.

The present invention provides a process for preparing 2,3-dihydro-2,2-dimethyl-7-hydroxybenzofuran which comprises subjecting o-methallyloxyphenol to a rearrangement and cyclization in the presence of, as a catalyst, aluminum halide and N-substituted aniline derivative of the formula

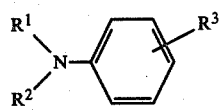

wherein $R^1$ and $R^2$ are each alkyl having 1 to 6 carbon atoms or phenyl, or are joined together to form alkylene having 5 to 7 carbon atoms, $R^3$ is hydrogen or alkyl having 1 to 3 carbon atoms, or a complex of both these compounds.

The above rearrangement and cyclization reactions are shown by the following reaction equations.

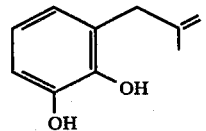

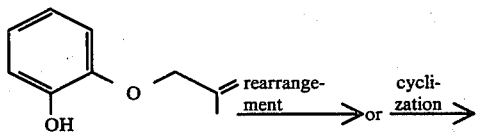

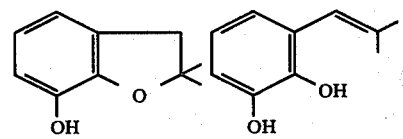

In the invention are used, as a catalyst, aluminum halide and N-substituted aniline derivative of the formula (1) or a complex of these compounds. The complex is usable as prepared in the reaction system by adding aluminum halide and N-substituted aniline derivative separately to the reaction system or as previously prepared. Examples of aluminum halide are aluminum iodide, aluminum bromide and aluminum chloride. The complex of aluminum halide and N-substituted aniline derivative can be prepared usually by employing about more than one mole of the latter per mole of the former. Aluminum iodide is usable in an amount of preferably about 0.001 to about 0.8 part by weight, more preferably about 0.008 to about 0.08 part by weight per part by weight of the monoether. Aluminum bromide and aluminum chloride are usable in an amount of preferably about 0.001 to about 0.5 part by weight, more preferably about 0.005 to about 0.05 part by weight per part by weight of the monoether. Aluminum halide is usable as containing crystal water but preferably used in the form of an anhydride. Suitable examples of N-substituted aniline derivatives of the formula (1) include N,N-dimethylaniline, N,N-diethylaniline, N-methyl-diphenylamine, N,N-dimethyl-p-toluidine and N-phenylpiperidine.

In the invention, the reaction is carried out preferably in the presence of a solvent. Useful solvents are N-substituted aniline derivative of the formula (1), aromatic hydrocarbon, aliphatic hydrocarbon, aromatic ether and aliphatic ether. Examples of preferable aromatic hydrocarbon are benzene, toluene, xylene, diethylbenzene, triethylbenzene, mesitylene, cumene, cymene, amylbenzene, naphthalene, tetralin and diphenylethane. Exemplary of aliphatic hydrocarbons include hexane, heptane, octane, nonane, decane, undecane, dodecane, tridecane, tetradecane, pentadecane, hexadecane, heptadecane and decalin. Examples of useful aromatic and aliphatic ethers are diphenyl ether, anisole, butyl phenyl ether and dibutyl cellosolve. The solvents can be used singly or in admixture with one another and is used usually in an amount of about 1 to about 50 parts by weight, preferably about 5 to about 25 parts by weight per part by weight of the monoether.

The reaction of the invention can be conducted usually at 60° to 250° C., preferably at 100° to 210° C. and can be carried out in any suitable manner, for example, in a batchwise or continuous manner.

Benzofuranol can be prepared from the monoether through the intermediate which is obtained by the rearrangement and is 3-methallyl-1,2-dihydroxybenzene or 3-isobutenyl-1,2-dihydroxybenzene. The present invention provides a process for preparing the benzofuranol in high yields by a simple one-step method directly from the monoether without separation or purification of the intermediate.

Further, as a great advantage of the invention, the reaction can be performed either at atmospheric or super-atmospheric pressure. It is possible to prepare the benzofuranol economically and in a high yield by a simple apparatus when the reaction is conducted at atmospheric pressure.

Given below are detailed embodiments of the invention. To the reactor can be added the monoether, catalyst and solvent in any order or can be added the monoether and solvent after forming the complex by mixing aluminum halide and N-substituted aniline derivative and the mixture is heated.

The reaction proceeds in a rapid reaction velocity and is completed usually in several ten minutes to several hours. After completion of the reaction, the benzofuranol can be isolated by a usual manner, for example, by a distillation and the like. Further, the benzofuranol can be used without isolation when employed as a starting material for preparing a further product.

For a better understanding of the invention Examples and Comparison Examples are given below.

EXAMPLE 1

Into a 300 ml glass reactor equipped with a thermometer, stirrer and reflux condenser was placed 200 g of N,N-dimethylaniline and nitrogen gas was introduced to replace the air in the reactor. When 0.4 g of aluminum bromide was added to the aniline with stirring, a complex was gradually formed.

To the solution was added 16.4 g (100 mM) of the monoether and the reaction was conducted at reflux temperature for 1 hour with stirring.

Analysis of the reaction mixture by high speed liquid chromatography showed a formation of 13.6 g (83 mM) of the benzofuranol. Further, the benzofuranol was identified by comparing NMR spectrum and mass spectrum of a fraction obtained from a distillation of the reaction mixture at a reduced pressure with those of an authentic substance.

EXAMPLES 2 TO 6

To the same reactor as used in Example 1 were added 16.4 g (100 mM) of the monoether, N-substituted aniline derivative and aluminum bromide with stirring under nitrogen atmosphere. The mixture was heated to react. The results were given in Table 1.

COMPARISON EXAMPLE 1

In the same manner as in Example 1, a reaction was conducted except that aluminum bromide was not used. Benzofuranol was obtained in a very low yield of 5%.

EXAMPLES 7 TO 10

To the same reactor as in Example 1 were added 16.4 g (100 mM) of monoether, N,N-dimethylaniline, solvent and aluminum bromide with stirring under nitrogen atmosphere. The mixture was heated to react. The results were shown in Table 2.

EXAMPLE 11

Into a 300 ml autoclave with glass lining equipped with a thermometer and stirrer were placed 16.4 g (100 mM) of monoether, 1.0 g of N,N-dimethylaniline, 100 g of mesitylene and 0.4 g of aluminum bromide under nitrogen atmosphere and the mixture was stirred and heated at 200° C. for 2 hours. Benzofuranol was obtained in 76% yield.

EXAMPLE 12

In the same manner as in Example 11, a reaction was conducted except that 100 g of toluene was used in place of mesitylene. Benzofuranol was obtained in 76% yield.

TABLE 2

| EX. | AlBr$_3$ (g) | N,N-Dimethyl-aniline (g) | Solvent | (g) | °C. × Hr | Yield (%) |
|---|---|---|---|---|---|---|
| 7 | 0.4 | 1.0 | Tetralin | 100 | 200 × 1 | 76 |
| 8 | 0.7 | 1.0 | Dibutyl cellosolve | 100 | 200 × 2 | 78 |
| 9 | 0.4 | 0.5 | n-dodecane | 200 | 200 × 2 | 78 |
| 10 | 0.4 | 0.5 | Diphenyl ether | 200 | 200 × 2 | 71 |

EXAMPLE 13

Into a 300 ml glass reactor equipped with a thermometer, stirrer and reflux condenser was placed 200 g of N,N-dimethylaniline and nitrogen gas was introduced to replace the air in the reactor. To the aniline was added 0.6 g of aluminum iodide and the mixture was stirred. To the mixture was added 16.4 g (100 mM) of monoether and the mixture was heated at reflux temperature for 1 hour with stirring.

Analysis of the reaction mixture by high speed liquid chromatography showed a formation of 13.8 g (84 mM) of benzofuranol.

TABLE 1

| EX. | AlBr$_3$ (g) | R$^1$ | R$^2$ | R$^3$ | Amount (g) | °C. × Hr | Yield (%) |
|---|---|---|---|---|---|---|---|
| 2 | 0.3 | CH$_3$— | CH$_3$— | H— | 100 | reflux × 0.5 | 80 |
| 3 | 0.5 | CH$_3$— | CH$_3$— | H— | 300 | 180 × 3 | 78 |
| 4 | 0.4 | CH$_3$— | CH$_3$— | p-CH$_3$— | 200 | 200 × 2 | 81 |
| 5 | 0.2 | C$_2$H$_5$— | C$_2$H$_5$— | H— | 200 | 200 × 2 | 80 |
| 6 | 0.4 | CH$_3$— |  | H— | 200 | 200 × 1 | 78 |

EXAMPLES 14 TO 18

To the same reactor as in Example 13 were added 16.4 g (100 mM) of monoether, N-substituted aniline derivatives and aluminum halide with stirring under nitrogen atmosphere. The mixture was heated to react and the results were given in Table 3.

TABLE 3

| EX. | $AlX_3$ | (g) | N—Substituted aniline derivtive | | | Amount (g) | °C. × Hr | Yield (%) |
|---|---|---|---|---|---|---|---|---|
| | | | $R^1$ | $R^2$ | $R^3$ | | | |
| 14 | $AlCl_3$ | 0.3 | $CH_3-$ | $CH_3-$ | H— | 100 | reflux × 0.5 | 76 |
| 15 | $AlI_3$ | 0.7 | $CH_3-$ | $CH_3-$ | H— | 300 | 180 × 3 | 79 |
| 16 | $AlI_3$ | 0.4 | $CH_3-$ | $CH_3-$ | p-$CH_3-$ | 200 | 200 × 2 | 82 |
| 17 | $AlCl_3 \cdot 6H_2O$ | 0.5 | $C_2H_5-$ | $C_2H_5-$ | H— | 200 | 200 × 2 | 71 |
| 18 | $AlI_3$ | 0.6 | $CH_3-$ | 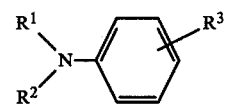 | H— | 200 | 200 × 1 | 80 |

EXAMPLES 19 TO 22

To the same reactor as in Example 13 were added 16.4 g (100 mM) of monoether, N,N-dimethylaniline, solvent and aluminum halide with stirring under nitrogen atmosphere. The mixture was heated to react and the results were given in Table 4.

EXAMPLE 23

Into a 300 ml autoclave with glass lining equipped with a thermometer and stirrer were placed 16.4 g (100 mM) of monoether, 1.0 g of N,N-dimethylaniline, 100 g of mesitylene and 0.5 g of aluminum iodide under nitrogen atmosphere and the mixture was stirred and heated at 200° C. for 2 hours. Benzofuranol was obtained in 78% yield.

EXAMPLE 24

In the same manner as in Example 23, a reaction was conducted except that 100 g of toluene was used in place of mesitylene. Benzofuranol was obtained in 78% yield.

TABLE 4

| EX. | $AlX_3$ | (g) | N,N—Dimethylaniline (g) | Solvent | (g) | °C. × Hr | Yield (%) |
|---|---|---|---|---|---|---|---|
| 19 | $AlCl_3$ | 0.2 | 1.0 | Tetralin | 100 | 200 × 1 | 74 |
| 20 | $AlI_3$ | 1.0 | 1.0 | Dibutyl cellosolve | 100 | 200 × 2 | 79 |
| 21 | $AlCl_3$ | 0.2 | 0.5 | n-dodecane | 200 | 200 × 2 | 76 |
| 22 | $AlI_3$ | 0.6 | 0.5 | Diphenyl ether | 200 | 200 × 2 | 73 |

We claim:

1. A process for preparing 2,3-dihydro-2,2-dimethyl-7-hydroxybenzofuran which comprises subjecting o-methallyloxyphenol to a rearrangement and cyclization in the presence of, as a catalyst, aluminum halide and N-substituted aniline derivative of the formula

(1)

wherein
$R^1$ and $R^2$ are each alkyl having 1 to 6 carbon atoms or phenyl, or are joined together to form alkylene having 5 to 7 carbon atoms,
$R^3$ is hydrogen or alkyl having 1 to 3 carbon atoms, or a complex of both these compounds.

2. A process as defined in claim 1 wherein the aluminum halide is aluminum iodide, aluminum bromide or aluminum chloride.

3. A process as defined in claim 1 wherein the N-substituted aniline derivative is N,N-dimethylaniline, N,N-diethylaniline, N-methyl-diphenylamine, N,N-dimethyl-p-toluidine or N-phenylpiperidine.

4. A process as defined in claim 1 wherein the N-substituted aniline derivative is used in an amount of more than one mole per mole of the aluminum halide.

5. A process as defined in claim 1 wherein the aluminum iodide is used in an amount of about 0.001 to about 0.8 part by weight per part by weight of o-methallyloxyphenol.

6. A process as defined in claim 1 wherein the aluminum bromide or aluminum chloride is used in an amount of about 0.001 to about 0.5 part by weight per part by weight of o-methallyloxyphenol.

7. A process as defined in claim 1 wherein as a solvent is used at least one compound selected from N-substituted aniline derivative of the formula (1), aromatic hydrocarbon, aliphatic hydrocarbon, aromatic ether and aliphatic ester.

8. A process as defined in claim 7 wherein the solvent is used in an amount of about 1 to about 50 parts by weight per part by weight of o-methallyloxyphenol.

9. A process as defined in claim 1 wherein the reaction is conducted at a temperature of about 60° to about 250° C.

10. A process as defined in claim 2 wherein the aluminum halide is aluminum bromide.

* * * * *